United States Patent
Schroeder

(10) Patent No.: US 7,078,561 B2
(45) Date of Patent: Jul. 18, 2006

(54) PREPARATION OF (METH)ACRYLIC ESTERS

(75) Inventor: Juergen Schroeder, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 11/177,299

(22) Filed: Jul. 11, 2005

(65) Prior Publication Data

US 2006/0030728 A1 Feb. 9, 2006

Related U.S. Application Data

(60) Provisional application No. 60/679,668, filed on May 11, 2005.

(30) Foreign Application Priority Data

Aug. 4, 2004 (DE) ...................... 10 2004 038 013

(51) Int. Cl.
*C07C 67/48* (2006.01)
(52) U.S. Cl. ..................................... 560/218
(58) Field of Classification Search ............... None
See application file for complete search history.

(56) References Cited

U.S. PATENT DOCUMENTS

| | | |
|---|---|---|
| 4,675,436 A | 6/1987 | Dietrich et al. |
| 4,889,950 A | 12/1989 | Bott et al. |
| 5,510,514 A | 4/1996 | Fauconet et al. |
| 5,945,560 A | 8/1999 | Iffland et al. |
| 6,172,258 B1 | 1/2001 | Jawaid et al. |
| 6,180,820 B1 | 1/2001 | Jawaid et al. |
| 6,353,130 B1 | 3/2002 | Aichinger et al. |

FOREIGN PATENT DOCUMENTS

| | | |
|---|---|---|
| DE | 196 04 252 A1 | 8/1997 |
| DE | 198 51 983 A1 | 5/2000 |
| EP | 0 202 610 A2 | 11/1986 |
| EP | 0 304 757 A1 | 3/1989 |
| EP | 0 609 127 A1 | 8/1994 |
| EP | 0 981 918 | 3/2000 |

*Primary Examiner*—Paul A. Zucker
(74) *Attorney, Agent, or Firm*—Oblon, Spivak, McClelland, Maier & Neustadt, P.C.

(57) ABSTRACT

A process for inhibiting polymerization in the preparation of (meth)acrylic esters of $C_1$–$C_8$-alcohols, wherein the pH of the water of reaction supplied to the $C_1$–$C_8$-alcohol recovery is greater than 7.

14 Claims, No Drawings

PREPARATION OF (METH)ACRYLIC ESTERS

The present invention relates to a process for inhibiting polymerization in the preparation of (meth)acrylic esters of $C_1$–$C_8$-alcohols.

In this document, the term (meth)acrylic acid is an abbreviation of methacrylic acid and/or acrylic acid, (meth)acrylic acid esters of methacrylic acid esters and/or acrylic esters.

The polymers or copolymer prepared on the basis of (meth)acrylic esters are of great economic significance in the form of polymer dispersions. They find use, for example, as adhesives, paints, or textile, leather and paper assistants.

(Meth)acrylic acid and (meth)acrylic esters are polymerizable compounds; therefore, sufficient polymerization inhibition has to be ensured in all process steps.

The preparation of (meth)acrylic esters has been described many times; see, for example, Kirk-Othmer, Encyclopedia of Chemical Technology, 4th edition, volume 1, pages 301 and 302, John Wiley & Sons, 1991.

DE 198 51 983 A1, just like EP 0 609 127 A1, describes processes for preparing (meth)acrylic esters in which the water of reaction is distilled azeotropically out of the reaction mixture. The crude ester is subsequently purified by extraction. Alcohol present in the aqueous phases is recycled into the process via an alcohol recovery.

DE 198 51 983 A1 additionally recommends the dissociation of the Michael addition products formed in the esterification and the recycling into the esterification.

EP 0 609 127 A1, in the preparation of butyl acrylate, additionally proposes the hydrolysis of the butylsulfuric acid present in the aqueous phase of the extraction stage to butanol and sulfuric acid. To prevent corrosion in the butanol recovery, the aqueous phase is neutralized after the hydrolysis.

DE 196 04 252 A1 and EP 0 984 918 B1 likewise describe processes in which the water of reaction is distilled azeotropically out of the reaction mixture. Subsequently, the ester is removed in a further distillation column by azeotropic distillation from unconverted acrylic acid and high boilers, for example esterification catalysts, polymerization inhibitors and Michael adducts. These processes too have an alcohol recovery.

Furthermore, U.S. Pat. No. 6,172,258 and U.S. Pat. No. 6,18,820 describe processes in which the water of reaction is distilled out of the reaction mixture together with butyl acrylate. These processes too have a butanol recovery.

A disadvantage of the aforementioned processes is that the aqueous phases removed still contain small amounts of (meth)acrylic acid and/or (meth)acrylic esters of $C_1$–$C_8$-alcohols. Undesired polymerization forms deposits therefrom. This polymerization can only be prevented insufficiently even when polymerization inhibitors are added.

It is thus an object to find a process for preparing (meth)acrylic esters of $C_1$–$C_8$-alcohols, in which the polymerization in the aqueous phases is prevented.

The object is achieved by a process for inhibiting polymerization in the preparation of (meth)acrylic esters of $C_1$–$C_8$-alcohols, wherein the pH of the water of reaction supplied to the $C_1$–$C_8$-alcohol recovery is greater than 7.

Generally, (meth)acrylic esters of $C_1$–$C_8$-alcohols are prepared by direct esterification of (meth)acrylic acid with $C_1$–$C_8$-alchols. The water released in the esterification is referred to in this document as water of reaction.

The processes known in the literature comprise several process steps which can, however, differ from one another in some variants.

In principle, a process for preparing (meth)acrylic esters of $C_1$–$C_8$-alcohols comprises the following steps:
 a) azeotropic esterification,
 b) removal of the water of reaction and
 c) recovery of the $C_1$–$C_8$-alcohol from the water of reaction.

Alternatively, the (meth)acrylic ester of $C_1$–$C_8$-alcohols can also be removed azeotropically between process steps b) and c), so that the process comprises the following steps:
 a) azeotropic esterification,
 b) removal of the water of reaction,
 c) azeotropic removal of the (meth)acrylic ester of $C_1$–$C_8$-alcohols and
 d) recovery of the $C_1$–$C_8$-alcohol from the water of reaction.

A further process variant for preparing (meth)acrylic esters of $C_1$–$C_8$-alcohols takes into account the dissociation of the Michael addition products and the recycling of the dissociation products into the esterification, so that this embodiment comprises the following process steps:
 a) azeotropic esterification
 b) removal of the water of reaction,
 c) recovery of the $C_1$–$C_8$-alkohol from the water of reaction,
 d) dissociation of the Michael addition products from the esterification residue and
 e) recycling of the dissociation products into the esterification.

Alternatively, the (meth)acrylic ester of $C_1$–$C_8$-alcohols may also be prepared by additionally azeotropically removing the ester:
 a) azeotropic esterification,
 b) removal of the water of reaction,
 c) azeotropic removal of the (meth)acrylic ester of $C_1$–$C_8$-alcohols,
 d) recovery of the $C_1$–$C_8$-alcohol from the water of reaction,
 e) dissociation of the Michael addition products from the esterification residue and
 f) recycling of the dissociation products into the esterification.

The process according to the invention for inhibiting polymerization in the azeotropic esterification of (meth)acrylic acid with $C_1$–$C_8$-alcohols by one of the abovementioned process variants has the feature that the pH of the water of reaction supplied to the $C_1$–$C_8$-alcohol recovery is greater than 7. The pH is preferably $\geq 7.5$, preferentially $\geq 8$, more preferably $\geq 8.5$ and in particular $\geq 9$.

The pH is set by adding in principle any customary alkaline substances, preferably alkali metal and alkaline earth metal compounds, for example sodium hydroxide, potassium hydroxide, sodium carbonate, potassium carbonate, sodium hydrogencarbonate, potassium hydrogencarbonate and/or calcium hydroxide. Preference is given to using sodium hydroxide, sodium carbonate and/or sodium hydrogencarbonate, more preferably as an aqueous solution. It should be noted that it is not possible to attain a pH of $\geq 9$ using hydrogencarbonates as the sole alkaline substances. The alkaline substances are therefore used as mixtures, but may also find use individually.

The alkaline substances may be metered in at any point, for example into the phase separator at the top of the esterification column, into the buffer vessel upstream of the $C_1$–$C_8$-alcohol recovery or into any pipeline.

As will be described in detail hereinbelow, sulfuric acid and/or sulfonic acids, for example p-toluenesulfonic acid, methanesulfonic acid and/or dodecylbenzenesulfonic acid, are frequently used in the preparation of (meth)acrylic esters of $C_1$–$C_8$-alcohols. The same catalysts are also used in the dissociation of the Michael addition products. Under the given reaction conditions, especially at the high temperatures of the dissociation, the catalysts decompose partly and release sulfur dioxide. This sulfur dioxide gets into the water of reaction and can be detected there.

The dissociation of the Michael addition products is described, for example, in EP 1 129 062 B1 and the literature cited there.

It is suspected that the released sulfur dioxide which functions as a redox initiator in water under acidic and neutral conditions is deactivated as a redox initiator in the alkaline range. This effectively prevents the polymerization, even though the water of reaction still contains traces of polymerizable compound.

Since the water of reaction is not corrosive, no special requirements have hitherto been made on the plant parts which conduct the water of reaction, for example lines or vessels. Typically, unalloyed steel was used. However, small amounts of iron ions are dissolved out of the unalloyed steel.

In extensive experiments, it has now been found that sulfur dioxide in conjunction with metal ions, especially iron ions, even in very small amounts, induces the polymerization of (meth)acrylic acid/(meth)acrylic ester mixtures in very dilute aqueous solutions. This is a problem especially when a buffer vessel is used as a reservoir for the recovery of the $C_1$–$C_8$-alcohol. In this buffer vessel, an organic upper phase can separate. The residence time of this upper phase which comprises polymerizable compounds in the buffer vessel is large, generally several days. Thus, the risk rises of an undesired polymerization.

In addition to the setting of the pH of the water of reaction fed to the $C_1$–$C_8$-alcohol recovery, further measures may therefore be taken to prevent or suppress the polymerization tendency in the aqueous phases.

These additional measures comprise the lines and/or vessels conducting the water of reaction a) comprising copper or b) consisting at least partly on the side facing the water of reaction of nonmetallic materials, copper or alloys.

The alloys mentioned under point b) contain at least 10% by weight, preferably at least 12.5% by weight, more preferably at least 15% by weight and in particular at least 16.5% by weight, of chromium, and at least 5% by weight, preferably at least 7.5% by weight, more preferably at least 9% by weight and in particular at least 10.5% by weight of nickel.

Copper likewise reduces the undesired polymerization in the water of reaction. Preference is given to using elemental copper. Copper may be introduced in any form into plant parts which conduct water of reaction, for example lines or vessels, for example as sheet metal or as metal turnings, or else the plant parts conducting water of reaction are manufactured at least partly from copper.

The plant parts conducting water of reaction, for example lines or vessels, may also be manufactured at least partly from stainless steel. Stainless steels are steels having a chromium content of at least 10% by weight, preferably at least 12.5% by weight, more preferably at least 15% by weight and in particular at least 16.5% by weight, of chromium, and a nickel content of at least 5% by weight, preferably at least 7.5% by weight, more preferably at least 9% by weight and in particular at least 10.5% by weight. The use of nonmetallic materials or linings, for example polytetrafluoroethylene or glass fiber-reinforced plastic, are likewise possible.

These measures constitute additional measures which, in addition to the pH adjustment, offer an additional means of polymerization inhibition in the aqueous phase of the (meth) acrylic ester preparation.

In the process according to the invention, $C_1$–$C_8$-alcohols are used to esterify the (meth)acrylic acid. It is typically possible to use any alcohol having from 1 to 8 carbon atoms, for example mono- or polyhydric alcohols, preferably mono- to tetrahydric alcohols, more preferably mono- to trihydric alcohols, even more preferably mono- or dihydric alcohols and in particular monohydric alcohols.

Examples are methanol, ethanol, n-propanol, isopropanol, n-butanol, sec-butanol, isobutanol, tert-butanol, ethylene glycol monomethyl ether, ethylene glycol monoethyl ether, diethylene glycol, 1,3-propanediol monomethyl ether, 1,2-propanediol, ethylene glycol, 2,2-dimethyl-1,3-propanediol, 1,3-propanediol, 1,2-butanediol, 1,4-butanediol, dimethylaminoethanol, n-hexanol, n-heptanol, n-octanol, 2-ethylhexanol, 3-methylpentane-1,5-diol, 2-ethylhexane-1,3-diol, 1,6-hexanediol, cyclopentanol, cyclohexanol, cyclooctanol, triethylene glycol, tetraethylene glycol, n-pentanol, trimethylolbutane, trimethylolpropane, trimethylolethane, pentaerythritol, 2-ethyl-1,3-propanediol, 2-methyl-1,3-propanediol, 2-ethyl-1,3-hexanediol, glycerol.

Preferred alcohols are methanol, ethanol, n-butanol, isobutanol, sec-butanol, 2-ethylhexanol, n-octanol and dimethylaminoethanol. Very particular preference is given to methanol, ethanol, n-butanol, 2-ethylhexanol and dimethylaminoethanol.

It is possible to use mixtures of a plurality of alcohols, for example 2 or 3, but preference is given to using only one alcohol.

(Meth)acrylic esters are prepared variously in a manner known per se by esterifying (meth)acrylic acid with an alcohol, for example an alkanol. (Meth)acrylic esters are obtained generally by homogeneously or heterogeneously catalyzed esterification, as described, for example, in Kirk Othmer, Encyclopedia of Chemical Technology, 4th ed., 1994, pages 301–302 and Ullmann's Encyclopedia of Industrial Chemistry, 5th edition, volume A1, pages 167–169.

In addition to the processes mentioned in the prior art, the literature includes numerous processes for preparing (meth) acrylic esters by esterifying (meth)acrylic acid with an alcohol, for example in German Laid-Open Specifications DE 196 04 252 A1 and DE 196 04 253 A1. A process for preparing butyl acrylate by acid-catalyzed esterification of acrylic acid with butanol is disclosed, for example, in WO 98/52904. EP 0 890 568 A1 is specified as an example of a batchwise acid-catalyzed esterification.

The acidic catalysts which can be used are preferably sulfuric acid, p-toluenesulfonic acid, benzenesulfonic acid, dodecylbenzenesulfonic acid, methanesulfonic acid or mixtures thereof, also conceivable are acidic ion exchangers or zeolites.

Particular preference is given to using sulfuric acid, p-toluenesulfonic acid and methanesulfonic acid; very particular preference is given to sulfuric acid and p-toluenesulfonic acid.

The catalyst concentration based on the reaction mixture is, for example, from 1 to 20% by weight, preferably from 5 to 15% by weight.

In the process according to the invention, stabilizers are used for polymerization inhibition. Suitable polymerization inhibitors are in principle any which are recommended for the stabilization of (meth)acrylic acid and (meth)acrylic esters, for example in DE 102 58 329 A1.

Suitable stabilizers may, for example, be N-oxides (nitroxyl or N-oxyl radicals, i.e. compounds which have at least one >N—O. group), for example 4-hydroxy-2,2,6,6-tetramethylpiperidine N-oxyl or 4-oxo-2,2,6,6-tetramethylpiperidine N-oxyl, phenols and naphthols, such as p-aminophenol, p-nitrosophenol, 2-tert-butylphenol, 4-tert-butylphenol, 2,4-di-tert-butylphenol, 2-methyl-4-tert-butylphenol, 2,6-tert-butyl-4-methylphenol or 4-tert-butyl-2,6-dimethylphenol, quinones, for example, hydroquinone or hydroquinone monomethyl ether, aromatic amines, for example N,N-diphenylamine, phenylenediamines, for example N,N'-dialkyl-p-phenylenediamine where the alkyl radicals may be the same or different and each independently consist of from 1 to 4 carbon atoms and may each be straight-chain or branched, for example N,N'-dimethyl-pphenylenediamine or N,N'-diethyl-p-phenylenediamine, hydroxylamines, for example N,N-diethylhydroxylamine, imines, for example methyl ethyl imine or methyl violet, sulfonamides, for example N-methyl-4-toluenesulfonamide or N-tert-butyl-4-toluenesulfonamide, oximes such as aldoximes, ketoximes or amide oximes, for example diethyl ketoxime, methyl ethyl ketoxime or salicyl aldoxime, phosphorus compounds, for example triphenyl phosphite or triethyl phosphite, sulfur compounds, metal salts, for example cerium(III) acetate or cerium(III) ethylhexanoate, or mixtures thereof.

Preference is given to stabilizing with hydroquinone, hydroquinone monomethyl ether, 4-hydroxy-2,2,6,6-tetramethylpiperidine N-oxyl, 4-oxo-2,2,6,6-tetramethylpiperidine N-oxyl, 2,6-tert-butyl-4-methylphenol or mixtures thereof.

Very particular preference is given to using 4-hydroxy-2,2,6,6-tetramethylpiperidine N-oxyl as the polymerization inhibitor.

The process according to the invention suppresses the polymerization in water of reaction of the (meth)acrylic ester preparation and thus increases the plant availability. It is thus suitable for all preparation processes of (meth)acrylic esters which are obtained by direct esterification.

ppm and percentage data used in this document relate, unless stated otherwise, to percentages and ppm by weight.

EXAMPLES

Example 1 to 10

0.5% by weight of butyl acrylate, 0.5% by weight of acrylic acid and 100 ppm by weight of sulfur dioxide, based in each case on the amount of water, were dissolved in water. In Examples 2, 4, 6, 8 and 10, the pH was adjusted to pH 9 using 5% by weight sodium hydroxide solution. In each case 70 ml of solution were stored with different additives at 80° C. in 100 ml screwed-lid bottles. The time up to opacity was measured, i.e. up to visible polymerization.

| Example | Additive | Time up to opacity [min] |
|---|---|---|
| 1 | Stainless steel sheet[1] | 5 |
| 2 | Steel sheet[1], pH 9 | >180 |
| 3 | Stainless steel sheet[2] | 3 |
| 4 | Steel sheet[2], pH 9 | >180 |
| 5 | Copper sheet | 65 |
| 6 | Copper sheet, pH 9 | >180 |
| 7 | Iron wire + copper sheet | 7 |
| 8 | Iron wire + copper sheet, pH 9 | >180 |
| 9 | Without additive | >180 |
| 19 | Without additive, pH 9 | >180 |

[1]Stainless steel sheet: 1.4571 material to DIN EN 10020, containing 16.5–18.5% by weight of chromium and 10.5–13.5% by weight of nickel
[2]Steel sheet: 1.0426 material to DIN EN 10020, unalloyed steel

What is claimed is:

1. A process for inhibiting polymerization in the preparation of (meth)acrylic esters of $C_1$–$C_8$-alcohols, comprising adjusting the pH of a water of reaction obtained by azeotropic distillation which is supplied to a $C_1$–$C_8$-alcohol recovery to be greater than 7.

2. The process according to claim 1, wherein the pH is ≧8.

3. The process according to claim 1 or 2, wherein the pH is ≧9.

4. The process according to any of claims 1 to 2, wherein the pH is adjusted with an alkaline substance selected from sodium hydroxide, sodium carbonate, sodium hydrogencarbonate and mixtures thereof.

5. The process according to claim 4, wherein the pH is adjusted using an aqueous solution of the alkaline substance.

6. The process according to any of claims 1 to 2, wherein the lines and/or vessels conducting the water of reaction comprise copper or at least partly at the side facing the water of reaction, consist of nonmetallic materials, copper or alloys.

7. The process according to claim 6, wherein the alloys contain at least 10% by weight of chromium and at least 5% by weight of nickel.

8. The process according to any of claims 1 to 2, wherein the water or reaction is conducted via a buffer vessel into the recovery of the $C_1$–$C_8$-alcohol.

9. The process of claim 1, comprising the following steps:
   a) azeotropic esterification;
   b) removal of said water of reaction; and
   c) recovery of said $C_{1-C8}$ alcohol from said water of reaction.

10. The process of claim 1, comprising the following steps:
   a) azeotropic esterification;
   b) removal of said water of reaction;
   c) azeotropic removal of a (meth)acrylic ester of $C_1$–$C_8$ alcohol; and
   d) recovery of said $C_1$–$C_8$ alcohol from said water of reaction.

11. The process of claim 1, comprising the following steps:
   a) azeotropic esterification;
   b) removal of said water of reaction;
   c) recovery of said $C_1$–$C_8$ alcohol from said water of reaction;
   d) dissociation of a Michael addition product from esterification residue; and
   e) recycling products of said dissociation into said esterification.

12. The process of claim 1, comprising the following steps:
   a) azeotropic esterification;
   b) removal of said water of reaction;
   c) azeotropic removal of a (meth)acrylic ester of $C_1$–$C_8$ alcohol;
   d) recovery of said $C_1$–$C_8$ alcohol from said water of reaction;
   e) dissociation of a Michael addition product from esterification residue; and
   f) recycling products of said dissociation into said esterification.

13. The process of claim 1, wherein preparation of said (meth)acrylic ester of $C_1$–$C_8$ alcohols is an acid-catalyzed esterification with an acid.

14. The process of claim 13, wherein said acid is at least one selected from the group consisting of sulfuric acid, p-toluensulfonic acid, benzenesulfonic acid, dodecylbenzenefulfonic acid, methanesulfonic acid, acidic ion exchanges, zeolites and a mixture thereof.

* * * * *